US00PP22105P2

(12) United States Plant Patent
Koot

(10) Patent No.: US PP22,105 P2
(45) Date of Patent: Sep. 6, 2011

(54) ***VACCINIUM* PLANT NAMED 'RED CANDY'**

(50) Latin Name: *Vaccinium vitis-idaea*
Varietal Denomination: Red Candy

(75) Inventor: Johannes Adrianus Maria Koot, Kaatsheuvel (NL)

(73) Assignee: Van Son & Koot Holding B.V., Kaatsheuvel (NL)

( * ) Notice: Subject to any disclaimer, the term of this patent is extended or adjusted under 35 U.S.C. 154(b) by 0 days.

(21) Appl. No.: 12/655,016

(22) Filed: Dec. 22, 2009

(51) Int. Cl.
*A01H 5/00* (2006.01)

(52) U.S. Cl. ..... Plt./156

(58) Field of Classification Search ..... Plt./156, Plt./226
See application file for complete search history.

(56) References Cited

PUBLICATIONS

UPOV-ROM GTITM, Plant Variety Database, 2010/6, GTI Jouve Retrieval Software, citation for 'Red Candy'.*

* cited by examiner

*Primary Examiner* — Susan McCormick Ewoldt
(74) *Attorney, Agent, or Firm* — Mark P. Bourgeois

(57) ABSTRACT

A new cultivar of *Vaccinium* plant named 'Red Candy' that is characterized by a compact habit, large dark red berries, numerous white flowers and a vigorous growth habit.

1 Drawing Sheet

Botanical classification: *Vaccinium vitis-idaea.*
Variety denomination: 'Red Candy'.

BACKGROUND OF THE INVENTION

The present invention relates to a new and distinct cultivar of *Vaccinium* plant botanically known as *Vaccinium vitis-idaea* and hereinafter referred to by the cultivar name 'Red Candy'.

The new cultivar is the product of a breeding program conducted by the inventor in a cultivated area of Kaatsheuvel, The Netherlands. The objective of the breeding program was to develop new *Vaccinium* cultivars with a compact habit, large numbers of flowers and large deep colored berries.

'Red Candy' is a hybrid that originated from the crossing of the female or seed parent an unnamed proprietary cultivar of *Vaccinium vitis-idaea* (not patented) and the male or pollen parent, *Vaccinium vitis-idaea* 'Aalshorse' (not patented) in 2004. The cultivar 'Red Candy' was selected by the inventor in 2006 as a single plant within the progeny of the stated cross in a controlled environment of Kaatsheuvel, The Netherlands.

Asexual reproduction by cuttings of the new cultivar 'Red Candy' was first performed in 2006 in Kaatsheuvel, The Netherlands. Since that time, under careful observation, the unique characteristics of the new *Vaccinium* cultivar have been uniform, stable and reproduced true to type in successive generations of asexual reproduction.

SUMMARY OF THE INVENTION

The following represent the distinguishing characteristics of the new *Vaccinium* cultivar 'Red Candy'. These traits in combination distinguish 'Red Candy' as a new and distinct cultivar apart from all other existing varieties of *Vaccinium* known to the inventor. 'Red Candy' has not been tested under all possible conditions and phenotypic differences may be observed with variations in environmental, climatic, and cultural conditions, however, without any variance in genotype.

1. *Vaccinium* 'Red Candy' exhibits a compact habit.
2. *Vaccinium* 'Red Candy' exhibits large dark red berries.
3. *Vaccinium* 'Red Candy' exhibits numerous white flowers.
4. *Vaccinium* 'Red Candy' exhibits a vigorous growth habit.

The closest comparison plant is *Vaccinium vitis-idaea* 'Koralle' (not patented) 'Red Candy' is distinguishable from 'Koralle' in having a more compact habit, a larger number of flowers that last over a longer time period, and larger berries.

The new cultivar 'Red Candy' is distinguishable from the unnamed female parent in having a more compact habit, a larger number of flowers, a longer flowering period and larger berries.

The new cultivar 'Red Candy' is distinguishable from the male parent 'Aalshorst' in having more flowers, a longer flowering period, a more vigorous habit and smaller berries. The berries of 'Aalshorst' are larger.

BRIEF DESCRIPTION OF THE DRAWING

The accompanying photograph illustrates the distinguishing traits of *Vaccinium* 'Red Candy'. The plant in the photograph shows an overall view of a four year old glass greenhouse grown plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Vaccinium* cultivar named 'Red Candy'. Data was collected in Kaatsheuvel, The Netherlands from four year old glass greenhouse grown plants. The time of year was September and the temperatures ranged from 12-32° Centigrade during the day, and 6-20° Centigrade during the night. The light level was natural outdoor light and there were no photoperiodic treatments or growth retardants used. Color determinations are in accordance with The Royal Horticultural Society Color Chart 2007 edition except where general color terms of ordinary dictionary significance are used. The growing requirements are similar to the species.

Botanical classification: *Vaccinium vitis-idaea* 'Red Candy'.

Type: Perennial shrub.

Use: Ornamental.

Parentage: 'Red Candy' is a hybrid plant that resulted from the following parent plants:

*Female parent.*—An unnamed proprietary cultivar of *Vaccinium vitis-idaea.*

*Male parent.*—*Vaccinium vitis-idaea* 'Aalshorse'.

Vigor: Moderate.

Growth rate: Moderate.

Growth habit: Broad upright.

Plant shape: Flattened globose.

Suitable container size: 13 cm.

Height: Average 17.3 cm. in height.

Width: Average 28.3 cm. in width.

Hardiness: USDA Zone 2.

Propagation: Softwood cuttings.

Time to initiate roots: Approximately 50 days are required to produce roots on an initial cutting.

Crop time: Approximately 22 months are required to achieve a finished plant from a rooted cutting.

Root system: Fine and fibrous, dense.

Stem:

*Branching habit.*—Free branching.

*Average number of lateral branches.*—56.

*Pinching.*—No.

*Lateral branch diameter.*—Average 2 mm. in diameter.

*Lateral branch length.*—Average 11.7 cm. in length.

*Stem strength.*—Strong.

*Stem color.*—Variable from 143C to 144A.

*Pubescence.*—Covered with dense soft hairs, 0.2 mm. in length, 191D in color.

*Internode length.*—Approximately 5 mm. between nodes.

*Shape.*—Rounded, slight glossy.

Foliage:

*Durability to foliage stress.*—High.

*Texture.*—Smooth and glossy.

*Leaf arrangement.*—Alternate.

*Compound or single.*—Single.

*Quantity of leaves per lateral branch.*—Average 23.

*Leaf shape.*—Elliptic to obovate.

*Leaf tip.*—Retuse.

*Leaf base.*—Attenuate.

*Leaf margin.*—Shallow serrate.

*Leaf length.*—2.1 cm.

*Leaf width.*—1.3 cm.

*Pubescence.*—Absent.

*Vein pattern.*—Pinnate.

*Leaf color young, upper surface.*—Between 141A and 143A.

*Leaf color young, lower surface.*—Between 143C and 144B.

*Leaf color mature, upper surface.*—Between N137A and 147A.

*Leaf color mature, lower surface.*—Between 146C and 146D.

*Vein color, upper side.*—144B.

*Vein color, under side.*—146C.

*Leaf attachment.*—Petiolate.

*Petiole dimensions.*—4.0 mm. in length and 1.0 mm. in width.

*Petiole color.*—144B.

Flower:

*Flower arrangement.*—Terminal and axillary raceme.

*Inflorescence type.*—Raceme.

*Inflorescence height.*—Average 5.5 cm. in height.

*Inflorescence diameter.*—Average 1.0 cm. in diameter.

*Quantity of flowers per inflorescence.*—Average 14.

*Flower type.*—Single.

*Flowering habit.*—Once a year.

*Quantity of flowers per lateral stem.*—Average 5.

*Quantity of flower buds per lateral stem.*—Average 23.

*Quantity of flowers and buds per plant.*—Average 1500.

*Flowering season.*—June to late September.

*Time to flower (response time).*—Approximately 9 months.

*Rate of flower opening.*—Approximately 20% of the flowers are opened at once.

*Fragrance.*—Faint, sweet.

*Flower bud length.*—Average 6.0 mm. in length.

*Flower bud diameter.*—Average 3 mm. in diameter.

*Flower bud shape.*—Elliptic.

*Bud color.*—NN155B, base 144A.

*Rate of bud opening.*—3 days.

*Flower aspect.*—Drooping.

*Flower shape.*—Urceolate.

*Flower dimensions.*—Average 6.5 mm. in diameter and 9.0 mm. in height.

*Flower longevity.*—Approximately 1 week.

*Petal appearance.*—Slightly glossy.

*Persistent or self-cleaning.*—Self-cleaning.

*Petal texture.*—Glabrous.

*Petal arrangement.*—Rotate.

*Number of petals.*—Four in number.

*Petals fused or unfused.*—Lower 2/3 fused.

*Petal shape.*—Obovate, tips reflexed.

*Petal margin.*—Entire.

*Petal apex.*—Broad acute.

*Petal dimensions.*—Average 6.0 mm. in length and 3.5 mm. in width.

*Petal color when opening (under side).*—NN155D.

*Petal color when opening (upper side).*—NN155D.

*Petal color fully opened (upper side).*—NN155D.

*Petal color fully opened (under side).*—NN155D.

*Petal color, fading to.*—NN155D with base tinges variable from red-purple 63C to grey-purple 186D.

*Petaloids.*—Absent.

*Sepal arrangement.*—Rotate.

*Number of sepals.*—Average 4.

*Sepal surface.*—Smooth, dull.

*Sepal shape.*—Triangulate.

*Sepal margin.*—Entire.

*Sepal apex.*—Acute.

*Sepal base.*—Broad cuneate.

*Sepal dimensions.*—Average 2.0 mm. in length and 1.5 mm. in width.

*Sepal color, young (upper side).*—144A.

*Sepal color, young (under side).*—144A.

*Sepal color, mature (upper side).*—144B.

*Sepal color, mature (under side).*—144B.

*Calyx shape.*—Rotate.

*Calyx dimensions.*—Average 2.0 mm. in length and 3.0 mm. in diameter.

*Peduncle dimensions.*—Average 4.8 cm. in length and 1.0 mm. in diameter.
*Peduncle angle.*—Central 0° , secondary 35° from vertical.
*Peduncle strength.*—Moderate to strong.
*Peduncle color.*—143B.
*Pedicel dimensions.*—Average 3.0 mm. in length and 0.5 mm. in diameter.
*Pedicel angle.*—80° from vertical.
*Pedicel strength.*—Moderate.
*Pedicel color.*—143B.

Reproduction organs:
*Stamen number.*—Average 16.
*Anther shape.*—Dorsifixed, oval.
*Anther dimensions.*—1.5 mm. in length; filament 1.5 mm. in length.
*Anther color.*—172A.
*Filament color.*—155A.
*Pollination requirements.*—Cross-pollination readily occurs between plants grown in proximity to each other.
*Amount of pollen.*—Low.
*Pollen color.*—N167C.
*Pistil number.*—One in number.
*Pistil length.*—7 mm.
*Stigma shape.*—Narrow club shaped.
*Stigma color.*—144B.
*Style length.*—6.5 mm.
*Style color.*—145D.
*Ovary color.*—143A.

Fruit:
*Use.*—Ornamental use only.
*Quantity of fruit per lateral branch.*—Average 28.
*Quantity of fruit per plant.*—Average 1500.
*Fruit shape.*—Spherical.
*Fruit diameter.*—1.2 cm.
*Fruit color.*—53A with blushes of 54B and 54C.
*Fruit texture.*—Smooth, glossy.
*Number of days to fruit ripening.*—Average 21 days.

Seed:
*Quantity of seeds per fruit.*—Average 40.
*Seed dimensions.*—Average 1.5 mm. in length and 0.5 mm. in diameter.
*Seed color.*—175B.

Disease and pest resistance: Has not been observed.

The invention claimed is:

1. A new and distinct variety of *Vaccinium* plant named 'Red Candy' as described and illustrated.

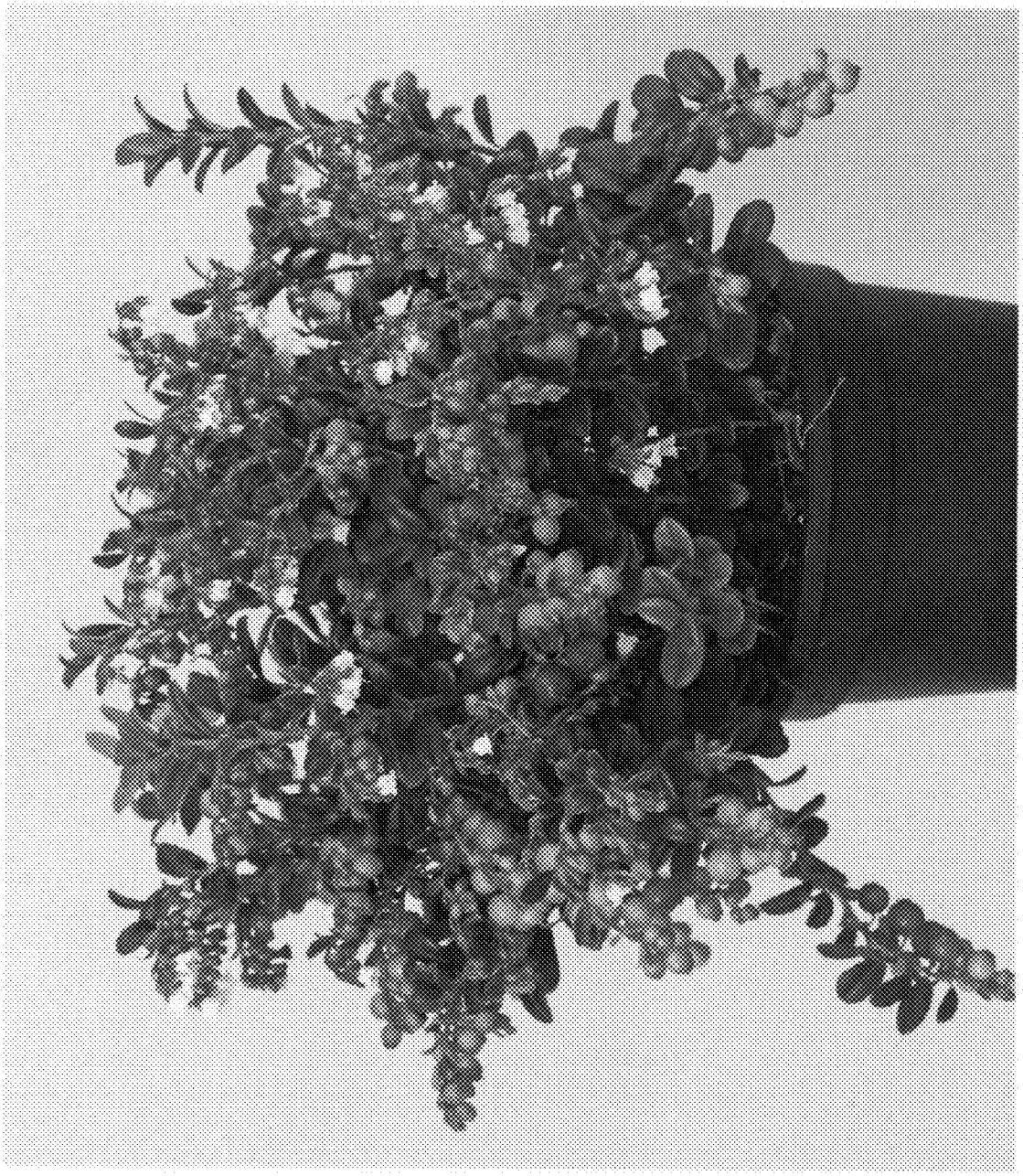

* * * * *